United States Patent
Mantzilas et al.

(10) Patent No.: US 11,452,999 B2
(45) Date of Patent: Sep. 27, 2022

(54) ISOTOPE PREPARATION METHOD

(71) Applicant: Bayer AS, Oslo (NO)

(72) Inventors: Dimitrios Mantzilas, Sorumsand (NO); Jan Roger Karlson, Oslo (NO); Judit Tjelmeland Østby, Kråkstad (NO)

(73) Assignee: Bayer AS, Oslo (NO)

( * ) Notice: Subject to any disclaimer, the term of this patent is extended or adjusted under 35 U.S.C. 154(b) by 30 days.

(21) Appl. No.: 16/897,994

(22) Filed: Jun. 10, 2020

(65) Prior Publication Data

US 2020/0406247 A1     Dec. 31, 2020

Related U.S. Application Data (63) Continuation of application No. 16/067,146, filed as application No. PCT/EP2016/082835 on Dec. 29, 2016, now abandoned.

(30) Foreign Application Priority Data

Jan. 5, 2016 (GB) .................................... 1600154

(51) Int. Cl.
| | | |
|---|---|---|
| *B01J 41/05* | (2017.01) | |
| *B01J 39/05* | (2017.01) | |
| *B01D 15/18* | (2006.01) | |
| *B01D 15/36* | (2006.01) | |
| *G21G 1/00* | (2006.01) | |
| *B01J 49/60* | (2017.01) | |
| *A61K 51/00* | (2006.01) | |

(52) U.S. Cl.
CPC ............... *B01J 41/05* (2017.01); *A61K 51/00* (2013.01); *B01D 15/1871* (2013.01); *B01D 15/362* (2013.01); *B01D 15/363* (2013.01); *B01J 39/05* (2017.01); *B01J 49/60* (2017.01); *G21G 1/001* (2013.01)

(58) Field of Classification Search
CPC ... B01J 39/05; B01J 41/05; B01J 41/08; B01J 2523/395; B01D 15/18; B01D 15/36
See application file for complete search history.

(56) References Cited

U.S. PATENT DOCUMENTS

| | | | |
|---|---|---|---|
| 5,809,394 A | 9/1998 | Bray et al. | |
| 2006/0228297 A1* | 10/2006 | Larsen | A61K 51/1096 534/11 |
| 2013/0136690 A1* | 5/2013 | Karlson | G21G 1/0005 423/2 |
| 2015/0292061 A1* | 10/2015 | Fassbender | C22B 60/0295 423/7 |

FOREIGN PATENT DOCUMENTS

EP     2564396 A1     3/2013

OTHER PUBLICATIONS

International Search Report dated Mar. 21, 2017 for PCT Application No. PCT/EP2016/082835, filed Dec. 29, 2016, 3 pages.

\* cited by examiner

*Primary Examiner* — Michael G. Hartley
*Assistant Examiner* — Jagadishwar R Samala
(74) *Attorney, Agent, or Firm* — Morrison & Foerster LLP (57) ABSTRACT

The present invention comprises a method for the generation of $^{227}$Th of pharmaceutically tolerable purity comprising
i) preparing a generator mixture comprising $^{227}$Ac, $^{227}$Th and $^{223}$Ra;
ii) loading said generator mixture onto a strong base anion exchange resin;
iii) eluting a mixture of said $^{223}$Ra and $^{227}$Ac from said strong base anion exchange resin using a first mineral acid in an aqueous solution;
iv) eluting $^{227}$Th from said strong base anion exchange resin using a second mineral acid in an aqueous solution whereby to generate a first $^{227}$Th solution containing contaminant $^{223}$Ra and $^{227}$Ac;
v) loading the first $^{227}$Th solution onto a strong acid cation exchange resin;
vi) eluting at least a part of the contaminant $^{223}$Ra and $^{227}$Ac from said strong acid cation exchange resin using a third mineral acid in aqueous solution; and
vii) eluting the $^{227}$Th from said strong acid cation exchange resin using a first aqueous buffer solution to provide a second $^{227}$Th solution.

Purified thorium-227 of pharmaceutical purity and a pharmaceutical composition comprising the same are also provided.

28 Claims, 2 Drawing Sheets

Figure 1 - Manufacturing process and process control

Figure 2

ISOTOPE PREPARATION METHOD

CROSS-REFERENCE TO RELATED APPLICATIONS

This application is a continuation application of U.S. patent application Ser. No. 16/067,146, which adopts the international filing date of Dec. 29, 2016, which is the National Phase application under 35 U.S.C. § 371 of International Application No. PCT/EP2016/082835, filed Dec. 29, 2016, which claims priority benefit to GB Application No. 1600154.7, filed Jan. 5, 2016.

FIELD OF THE INVENTION

The present invention relates to the preparation of thorium-227 ($^{227}$Th), such as thorium-227 chloride, for pharmaceutical use. In particular, the present invention relates to methods for potentially commercial-scale production of thorium-227 having a purity acceptable for pharmaceutical administration to human subjects.

BACKGROUND OF THE INVENTION

Specific cell killing can be essential for the successful treatment of a variety of diseases in mammalian subjects. Typical examples of this are in the treatment of malignant diseases such as sarcomas and carcinomas. However the selective elimination of certain cell types can also play a key role in the treatment of many other diseases, especially immunological, hyperplastic and/or other neoplastic diseases.

The most common methods of selective treatment are currently surgery, chemotherapy and external beam irradiation. Targeted endo-radionuclide therapy is, however, a promising and developing area with the potential to deliver highly cytotoxic radiation to unwanted cell types. The most common forms of radiopharmaceutical currently authorised for use in humans employ beta-emitting and/or gamma-emitting radionuclides. There has, however, been a recent surge in interest in the use of alpha-emitting radionuclides in therapy because of their potential for more specific cell killing. One alpha-emitting nuclide in particular, radium-223 ($^{223}$Ra) has proven remarkably effective, particularly for the treatment of diseases associated with the bone and bone-surface. Additional alpha-emitters are also being actively investigated and one isotope of particular interest is the alpha-emitter thorium-227.

The radiation range of typical alpha emitters in physiological surroundings is generally less than 100 micrometers, the equivalent of only a few cell diameters. This makes these nuclei well suited for the treatment of tumours, including micrometastases, because little of the radiated energy will pass beyond the target cells and thus damage to surrounding healthy tissue might be minimised (see Feinendegen et al., Radiat Res 148:195-201 (1997)). In contrast, a beta particle has a range of 1 mm or more in water (see Wilbur, Antibody Immunocon Radiopharm 4:85-96 (1991)).

The energy of alpha-particle radiation is high compared to beta particles, gamma rays and X-rays, typically being 5-8 MeV, or 5 to 10 times that of a beta particle and 20 or more times the energy of a gamma ray. Thus, this deposition of a large amount of energy over a very short distance gives α-radiation an exceptionally high linear energy transfer (LET), high relative biological efficacy (RBE) and low oxygen enhancement ratio (OER) compared to gamma and beta radiation (see Hall, "Radiobiology for the radiologist", Fifth edition, Lippincott Williams & Wilkins, Philadelphia Pa., USA, 2000). These properties explain the exceptional cytotoxicity of alpha emitting radionuclides and also impose stringent demands on the level of purity required where an isotope is to be administered internally. This is especially the case where any contaminants may also be alpha-emitters, and most particularly where long half-life alpha emitters may be present, since these can potentially be retained in the body, causing significant damage over an extended period of time.

The radioactive decay chain from $^{227}$Ac, generates $^{227}$Th and then leads to $^{223}$Ra and further radioactive isotopes. The first three isotopes in this chain are shown below. The table shows the element, molecular weight (Mw), decay mode (mode) and Half-life (in years (y) or days (d)) for $^{227}$Th and the isotopes preceding and following it. Preparation of $^{227}$Th can begin from $^{227}$Ac, which is itself found only in traces in uranium ores, being part of the natural decay chain originating at $^{235}$U. One ton of uranium ore contains about a tenth of a gram of actinium and thus although $^{227}$Ac is found naturally, it is more commonly made by the neutron irradiation of $^{226}$Ra in a nuclear reactor.

Figure 1:
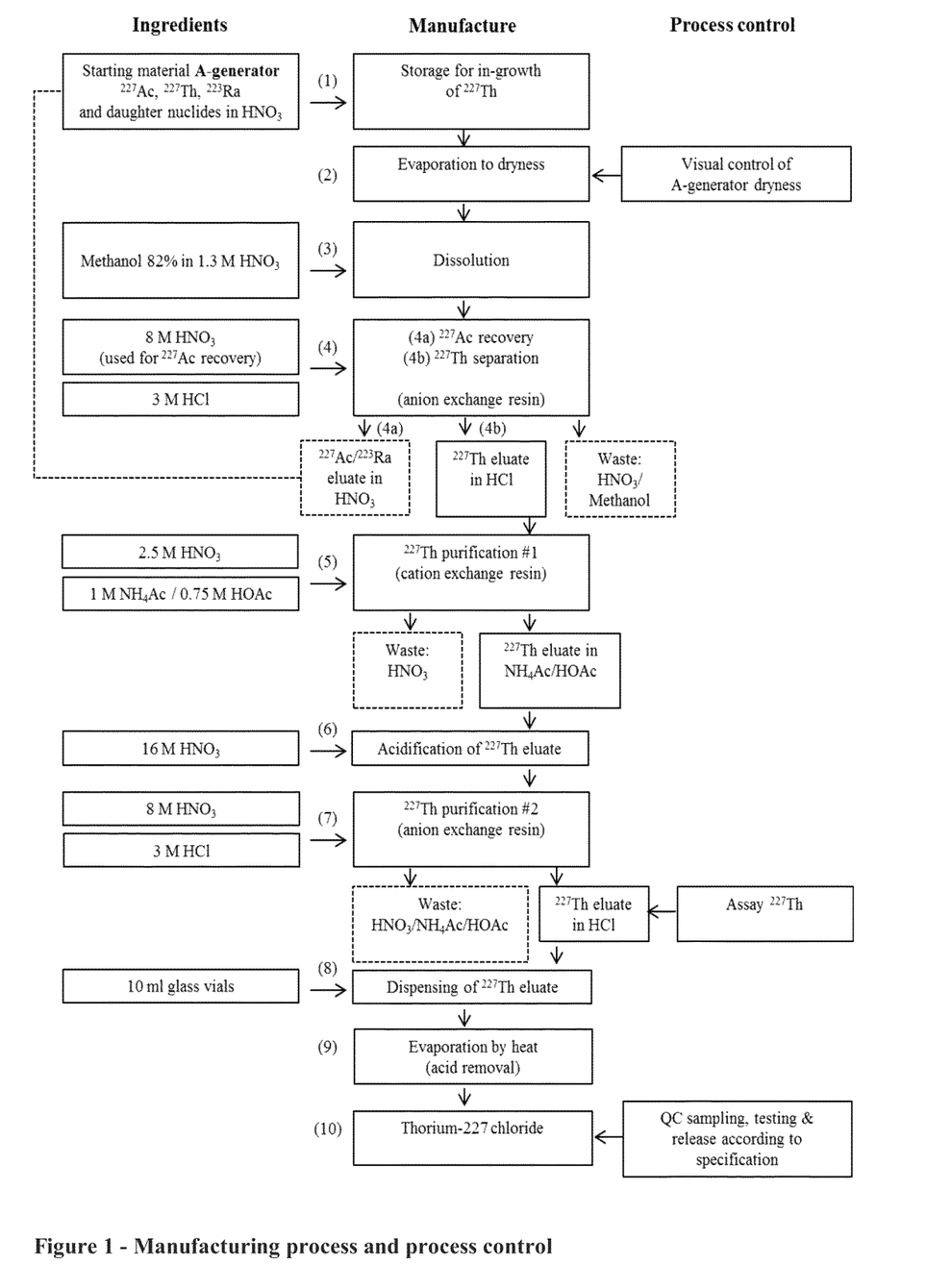
FIG. 1 Shows a typical manufacturing process and control, comprising an embodiment of the method of the present invention including several optional steps.
Figure 2:
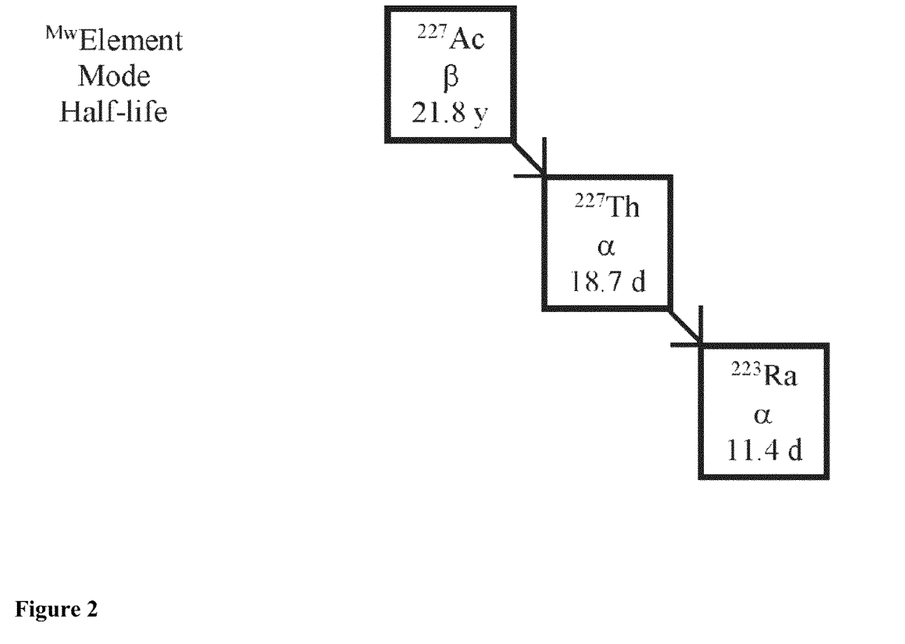
FIG. 2 shows that $^{227}Ac$, with a half-life of over 20 years, is a very dangerous potential contaminant with regard to preparing $^{227}Th$ from the above decay chain for pharmaceutical use.

It can be seen from FIG. 2 that $^{227}$Ac, with a half-life of over 20 years, is a very dangerous potential contaminant with regard to preparing $^{227}$Th from the above decay chain for pharmaceutical use. In particular, although $^{227}$AC itself is a beta-emitter, its long half-life means that even very low activities represent a significant lifetime radiation exposure, and furthermore, once it decays, the resulting daughter nuclei (i.e. $^{227}$Th) generate a further 5 alpha-decays and 2 beta-decays before reaching stable $^{207}$Pb. These are illustrated in the table below:

| | Nuclide | | | | | | | |
|---|---|---|---|---|---|---|---|---|
| | $^{227}$Th | $^{223}$Ra | $^{219}$Rn | $^{215}$Po | $^{211}$Pb | $^{211}$Bi | $^{207}$Tl | $^{207}$Pb |
| ½-life | 18.7 d | 11.4 d | 4.0 s | 1.8 ms | 36.1 m | 2.2 m | 4.8 m | stable |
| α-energy/MeV | 6.15 | 5.64 | 6.75 | 7.39 | | 6.55 | | |
| β-energy (max)/MeV | | | | | 1.37 | | 1.42 | |
| Energy % | 17.5 | 16.0 | 19.1 | 21.0 | 3.9 | 18.6 | 4.0 | |

It is evident from the above two decay tables that more than 35 MeV of energy is deposited by one $^{227}$Ac decay chain, representing a significant toxicity risk for essentially the entire lifetime of any human subject administered with $^{227}$Ac. As a result, the content of $^{227}$Ac contaminant in $^{227}$Th for pharmaceutical use is recommended to be limited to 0.002% Ac$^{227}$ (i.e. no more than 200 Bq $^{227}$Ac in 1 MBq $^{227}$Th). Thus for practical purposes, a method which is to provide $^{227}$Th for pharmaceutical use should preferably provide a purity of better than 200 Bq $^{227}$Ac in 1 MBq $^{227}$Th, preferably better than 100 or better than 50 Bq $^{227}$Ac in 1 MBq $^{227}$Th. Most suitable methods will aim to provide a purity of 20 Bq $^{227}$Ac in 1 MBq $^{227}$Th or better (e.g. 1 to 20 Bq $^{227}$Ac in 1 MBq $^{227}$Th), preferably less than 20 Bq $^{227}$Ac in 1 MBq $^{227}$Th, more preferably less than 10 Bq $^{227}$Ac in 1 MBq $^{227}$Th to ensure that the safety limit is always adhered to.

Previously known preparations for $^{227}$Th have generally been for small quantities and/or not tested for purity to pharmaceutical standards. In WO2004/091668, for example, $^{227}$Th was prepared by anion exchange from a single column and used for experimental purposes without validation of the purity.

No previously known method for the generation of $^{227}$Th addresses issues such as yield of $^{227}$Th, speed of the purification process, automation, minimising of wasted isotopes and corresponding production of radioactive waste or any similar issues associated with clinical and/or commercial-scale production. Furthermore, few methods attempt to measure and validate the purity with respect to $^{227}$Ac contamination.

In view of the above, there is a considerable need for an improved method by which $^{227}$Th may be generated and purified for pharmaceutical use at a purity appropriate for direct injection into human subjects. It would be a considerable advantage if the method were to provide a high yield of $^{227}$Th, a low loss of $^{227}$Ac parent isotopes and/or utilise widely available separation media. It would be further advantageous if the method was rapid, was viable for relatively large (clinical/commercial scale) radioactive samples, included only a minimum number of manual handling steps, and/or was suitable for automation.

BRIEF DESCRIPTION OF THE INVENTION

The present inventors have now established that by separation of a $^{227}$Ac/$^{227}$Th generator (containing also $^{223}$Ra and its daughter isotopes) using a strong base anion exchange resin, followed by separation utilising a strong acid cation exchange resin, a $^{227}$Th solution of very high radiochemical purity may be produced while providing a number of desirable advantages in the method. It is preferable that the $^{227}$Th is generated as, or converted to, at least one pharmaceutically acceptable salt form. Thorium-227 chloride is preferred in this respect.

In a first aspect, the present invention therefore provides a method for the generation of $^{227}$Th of pharmaceutically tolerable purity comprising i) preparing a generator mixture comprising $^{227}$Ac; $^{227}$Th and $^{223}$Ra;

ii) loading said generator mixture onto a strong base anion exchange resin;

iii) eluting a mixture of said $^{223}$Ra and $^{227}$Ac from said strong base anion exchange resin using a first mineral acid in an aqueous solution;

iv) eluting $^{227}$Th from said strong base anion exchange resin using a second mineral acid in an aqueous solution whereby to generate a first $^{227}$Th solution containing contaminant $^{223}$Ra and $^{227}$Ac;

v) loading the first $^{227}$Th solution onto a strong acid cation exchange resin;

vi) optionally eluting the contaminant $^{223}$Ra and $^{227}$Ac from said strong acid cation exchange resin using a third mineral acid in aqueous solution; and vii) eluting the $^{227}$Th from said strong acid cation exchange resin using a first aqueous buffer solution to provide a second $^{227}$Th solution.

The process will optionally and preferably also include a second anion exchange separation comprising the steps of:

viii) loading the second $^{227}$Th solution eluted in step vii) (or the $^{227}$Th therefrom) onto a second strong base anion exchange resin;

ix) optionally eluting any remaining $^{223}$Ra and $^{227}$Ac from said second strong base anion exchange resin using a fourth mineral acid in an aqueous solution; and x) eluting $^{227}$Th from said second strong base anion exchange resin using a fifth mineral acid in an aqueous solution.

Steps vi) and ix) of the above methods relate to optional steps. In these methods, contaminant $^{223}$Ra and/or $^{227}$Ac will preferably be eluted and may be recycled or disposed of as waste. In an alternative embodiment, however, steps vi) and/or ix) may be omitted and contaminant $^{223}$Ra and/or $^{227}$Ac retained on the resin when the $^{227}$Th is eluted.

The process will typically include recovery of the $^{227}$Ac eluted in step iii) and may additionally comprise the step of:

y) storing the $^{227}$Ac eluted in step iii) for a period sufficient to allow ingrowth of $^{227}$Th by radioactive decay, whereby to regenerate a generator mixture comprising $^{227}$Ac, $^{227}$Th and $^{223}$Ra.

After ingrowth step y), the generator mixture may be re-used to generate a further batch of $^{227}$Th, and a single $^{227}$Ac sample will preferably be used repeatedly (e.g. more than 10 times, such as 50 to 500 times). Evidently, where a useful amount of $^{227}$Ac is eluted in step vi), this may also be recovered and returned to the generator.

In a further aspect, the present invention provides a solution of $^{227}$Th comprising less than 20 Bq $^{227}$Ac per 1 MBq $^{227}$Th, preferably a solution of $^{227}$Th comprising less than 20 Bq $^{227}$Ac in 1 MBq $^{227}$Th (e.g. 1 to 20 Bq $^{227}$Ac in 1 MBq $^{227}$Th), preferably less than 200 Bq $^{227}$Ac in 1 MBq $^{227}$Th, more preferably less than 10 Bq $^{227}$Ac in 1 MBq $^{227}$Th. Such a solution is optionally formed or formable by any of the methods herein described, and is preferably formed or formable by the preferred methods herein described. Correspondingly, the methods of the invention are preferably for the formation of a solution of $^{227}$Th comprising less than 10 Bq $^{227}$Ac in 1 MBq $^{227}$Th (e.g. 1 to 20 Bq $^{227}$Ac in 1 MBq $^{227Th}$), preferably less than 20 Bq $^{227}$Ac in 1 MBq $^{227}$Th, more preferably less than 15 Bq $^{227}$Ac in 1 MBq $^{227}$Th.

DETAILED DESCRIPTION OF THE INVENTION

A very significant aspect of the present invention is the ability for the $^{227}$Ac of the generator mixture to be stripped from the separation resin and regenerated with high efficiency. In particular, the present method relates to a process for long-term clinical/commercial use, and as such should be capable of allowing the repeated use of the generator mixture for many years. The useful life of the generator mixture will certainly be of the order of the half-life of the originating $^{227}$Ac isotope, and thus potentially several tens of years (e.g. 10 to 50 years). There are several issues which result from this which have not been addressed in any of the $^{227}$Th production or purification systems previously described.

A first issue arising from the potentially long clinical/commercial lifetime of the generator mixture is the stability of its storage environment. Specifically, any material exposed to the generator mixture is potentially receiving more than a million beta decays per second from the $^{227}$Ac, plus around the same number of alpha decays per second from the included $^{227}$Th and up to the same number of alpha decays again from the in-growing $^{223}$Ra and from each of its alpha-emitting daughter nuclides. This is very much more concentrated than any $^{227}$Th generator/separation system previously analysed in any detail.

Alpha irradiation in particular is highly ionising and so over the course of a number of years, the $10^{13}$ or more alpha-decays per year to which the surroundings of the generator will be exposed is very likely to cause significant damage to any organic components in long term proximity. As a result, it will be desirable that the originating $^{227}$Ac is not retained on the column but is re-generated so that a new column may be utilised as often as necessary or convenient (e.g. at each separation).

Periodic replacement of the separation materials not only avoids loss of the generator mixture but also guarantees that the purity of the product will be as high after several decades as it was when the system was first employed since the retention properties of the separation medium will not be degraded. The generator system will thus be recovered from the separation material after every use and may be stored as a solution or evaporated to dryness (or to a concentrated solution) for storage.

Where a generator mixture is recovered from a separation medium it is important that this happen to a very high degree. The loss of only 0.1% of the generator isotope would be entirely insignificant in any laboratory or testing environment, but for a clinical/commercial system is an important factor. Assuming that the generator is used every 3rd week, then regeneration of the $^{227}$Ac occurs 17 times a year. At a 0.1% loss each time, this would result in a total loss of 12% of the original $^{227}$Ac over a 10 year period. This, combined with the natural decay loss due to the 21 year half-life of the isotope increases the total reduction in activity from 73% (of the original activity) due to natural decay down to 61% including the regeneration loss. At 21.8 years, this effect is still more dramatic, taking the 50% activity expected after one half-life down to approximately 35% and evidently reducing the useful commercial life of the system by this stage.

In the present method, the regeneration of the generator mixture has been shown to lose only not more than 0.05% of the original $^{227}$Ac at each regeneration cycle. Preferably this will be achievable by recovering $^{227}$Ac at only one point in the process (step iii)). If necessary, $^{227}$Ac recovered at other steps may be included, however.

The regeneration step iii) will typically have the following features:
  a) The first mineral acid may be any mineral acid or mixture thereof, but will preferably comprise nitric acid. The first mineral acid may comprise, consist essentially of or consist of an acid selected from $H_2SO_4$, $HNO_3$ and mixtures thereof and will preferably comprise, consist essentially of or consist of $HNO_3$ in aqueous solution.
  b) The first mineral acid may be used at a concentration of 0.1 to 12M, preferably 1 to 12M, more preferably 6 to 10M (e.g. around 8M).

With regard to optional but highly preferable step y), the regeneration of the $^{227}$Th will begin by natural radioactive decay as soon as the existing $^{227}$Ac is eluted in step iii). It is preferable to allow sufficient time for significant ingrowth of $^{227}$Th before the generator mixture is again separated, and the period which is suitable will depend upon the quantity of $^{227}$Ac present and the quantity of $^{227}$Th which it is desired to separate in each batch. Eventually, the level of activity of each isotope in the decay chain will equilibrate and further storage will achieve little or no enhancement in $^{227}$Th content. Thus to minimise the separation effort required, longer storage will be used while to maximise the recovery of useful $^{227}$Th, frequent separation will be undertaken. Typically the storage time will be commensurate with the half-life of the $^{227}$Th (~19 days) and so storage step y) may be undertaken for around 5 to 100 days, preferably around 10 to 50 days. Frequent separation (e.g. daily) may be undertaken if it is desired to maximise the yield of separated $^{227}$Th from the generator. The skilled worker will have no difficulty selecting a suitable ingrowth period based upon the characteristics of each particular system.

The present invention provides a method for the production of $^{227}$Th at a purity suitable for use in endo-radionuclide therapy. A number of preferred features of the system are indicated below, each of which may be used in combination with any other feature where technically viable, unless indicated otherwise.

The methods and all corresponding embodiments of the invention will preferably be carried out on a clinical/commercial scale and thus will be capable and suitable for use at this scale while maintaining all of the other characteristics described herein as appropriate (such as radionuclear purity, optionally methanol content etc). A commercial scale will typically be a scale greater than that required for the treatment of a single subject, and may be, for example, the purification of more than 10, preferably more than 25 and most preferably more than 45 typical doses of $^{227}$Th. Evidently, a typical dose will depend upon the application, but anticipated typical dose may be from 0.5 to 200 MBq or 0.5 to 100 MBq, preferably 1 to 75 MBq, most preferably around 2 to 50 MBq.

Step i) of the method of the invention relates to preparing a generator mixture comprising $^{227}$Ac, $^{227}$Th and $^{223}$Ra. Such a mixture will inherently form by the gradual decay of a sample of $^{227}$Ac, but for use in the invention will preferably also have one or more of the following features, either individually or in any viable combination:
  a) a $^{227}$Ac radioactivity of at least 500 MBq (e.g. 500 MBq to 50 GBq), preferably at least 1 GBq, more preferably at least 2.5 GBq;
  b) a $^{223}$Ra radioactivity of at least 25 MBq or at least 100 MBq (e.g. 100 MBq to 50 GBq), preferably at least 800 MBq, more preferably at least 1.5 GBq;
  c) a volume of no more than 100 ml (e.g. 0.1 to 10 ml), preferably no more than 50 ml, more preferably no more than 10 ml.
  d) a $^{227}$Th radioactivity of at least 25 MBq, at least 50 MBq or at least 100 MBq (e.g. 100 MBq to 50 GBq), preferably at least 800 MBq, more preferably at least 1.5 GBq;

The generator may be stored as a solution or in dry form. Where the generator is stored in solution, this will typically be evaporated and re-dissolved during loading step ii).

Step ii) of the method of the invention relates to the loading of the generator mixture onto a strong base anion exchange resin. This step and the entities referred to therein may have the following preferable features, either individually or in any viable combination, and optionally in any viable combination with any of the features of the other steps as described herein:
  a) The strong base anion exchange resin may be a polystyrene/divinyl benzene copolymer based resin, preferably containing 1-95%; divinyl benzene
  b) The strong base anion exchange resin may be an $R-N^+Me_3$ type (type I) resin or an $R-N^+Me_2CH_2CH_2OH$ (Type II) resin, preferably a type I resin;

c) The strong base anion exchange resin may have an exchange capacity of 0.2 to 5 meq/ml, preferably 0.6 to 3 meq/ml, most preferably 1 to 1.5 meq/ml (e.g. around 1.2 meq/ml);
d) The strong base anion exchange resin may have a particle size grading of 10 to 800 mesh, preferably 50 to 600 mesh, more preferably 100 to 500 mesh (e.g. around 200 to 400 mesh).
e) The strong base anion exchange resin may be used in the form of a column.
f) The volume of resin used (e.g. when packed in a column) may be 10 ml or less, (e.g. 0.1 to 10 ml), preferably 5 ml or less, more preferably 0.1 to 1 (e.g. around 0.25 ml).
g) The strong base anion exchange resin may be DOWEX 1X8 (e.g. DOWEX AG 1X8) or equivalent resin and may optionally and preferably have a 200-400 mesh size.
h) The generator may be evaporated to dryness and re-dissolved in a loading solution.
i) The loading solution may comprise a mineral acid, preferably $HNO_3$.
j) The mineral acid in the loading solution may be at a concentration of 0.1 to 5M, preferably 0.5 to 3M, more preferably 1 to 2 M.
k) The loading solution may comprise at least one alcoholic solvent.
l) The alcoholic solvent may comprise or consist of an alcohol selected from methanol, ethanol, n-propanol, i-propanol and mixtures thereof, preferably methanol.
m) The alcoholic solvent may be an aqueous alcohol or mixture thereof at a concentration of 30 to 95%, preferably 50 to 90%, more preferably 75 to 88% (e.g. around 82%).

Step iii) of the method of the invention relates to eluting a mixture of said $^{223}$Ra and $^{227}$Ac from the strong base anion exchange resin using a first mineral acid in aqueous solution. This step and the entities referred to therein may have the following preferable features, either individually or in any viable combination, and optionally in any viable combination with any of the features of the other steps as described herein:

a) The first mineral acid may be an acid selected from $H_2SO_4$ or $HNO_3$ preferably $HNO_3$.
b) The first mineral acid may be used at a concentration of 1 to 12M, such as 3 to 10 M or 5 to 9 M, preferably 7 to 8.5 M (e.g. around 8M), particularly where the first mineral acid is $HNO_3$.
c) The aqueous solution may be free or substantially free of any alcohol. In particular, the aqueous solution may contain less than 1% (e.g. 0 to 1%) of any alcohol selected from methanol, ethanol and isopropanol, particularly methanol;
d) The mixture of said $^{223}$Ra and $^{227}$Ac may be eluted from said strong base anion exchange resin using 1 to 200 column volumes of the first mineral acid in aqueous solution. Preferably the amount will be 5 to 100 column volumes (e.g. around 50 column volumes).

Step iv) of the method of the invention relates to eluting $^{227}$Th from said strong base anion exchange resin using a second mineral acid in an aqueous solution whereby to generate a first $^{227}$Th solution (typically containing low levels of contaminant $^{223}$Ra and $^{227}$Ac). This step and the entities referred to therein may have the following preferable features, either individually or in any viable combination, and optionally in any viable combination with any of the features of the other steps as described herein:

a) The second mineral acid may be an acid selected from $H_2SO_4$ and HCl, preferably HCl.
b) The second mineral acid may be used at a concentration of 0.1 to 8M, preferably 0.5 to 5M, more preferably 2 to 4M, most preferably around 3M. This applies particularly where the second mineral acid is HCl.
c) The first $^{227}$Th solution may be eluted from said strong base anion exchange resin using 1 to 200 column volumes of the second mineral acid in aqueous solution. Preferably the amount will be 5 to 100 column volumes (e.g. around 50 column volumes).
d) The aqueous solution may be free or substantially free of other solvents such as alcoholic solvents.
e) The first $^{227}$Th solution will preferably have a contamination level of no more than 100 (e.g. 1 to 100) Bq $^{227}$Ac per 1 MBq $^{227}$Th, more preferably no more than 45 Bq $^{227}$Ac per 1 MBq $^{227}$Th (e.g. no more than 30) and most preferably no more than 10 Bq $^{227}$Ac per 1 MBq $^{227}$Th.
f) The steps ii) to iv) of loading the generator mixture onto the base anion exchange resin, eluting a mixture of said $^{223}$Ra and $^{227}$Ac and a first $^{227}$Th solution may provide a separation ratio of $^{227}$Th to $^{227}$Ac of at least 10,000:1 (e.g. 10,000:1 to 500,000:1), preferably at least 20,000:1, more preferably at least 30,000:1.
g) The $^{227}$Th may be eluted from said strong base anion exchange resin in uncomplexed form, such as in the form of a simple salt in solution (e.g. as the salt of the second mineral acid, such as the chloride salt).
h) Optionally, the use of complexing agents such as DTPA may be avoided, and in one embodiment all solutions used in steps ii to iv) are substantially free of complexing agents, such as DTPA.

Step v) of the method of the invention relates to loading the first $^{227}$Th solution eluted from the anion exchange resin in step iv) onto a strong acid cation exchange resin. This step and the entities referred to therein may have the following preferable features, either individually or in any viable combination, and optionally in any viable combination with any of the features of the other steps as described herein:

a) The strong acid cation exchange resin may be a polystyrene/divinyl benzene copolymer based resin, preferably containing 1-95 DVB;
b) The strong acid cation exchange resin may be an $SO_3H$ type.
c) The strong acid cation exchange resin may have an exchange capacity of 0.2 to 5 meq/ml, preferably 0.6 to 3 meq/ml, most preferably 1 to 2 meq/ml (e.g. around 1.7 meq/ml);
d) The strong acid cation exchange resin may have a particle size grading of 10 to 800 mesh, preferably 50 to 600 mesh, more preferably 100 to 500 mesh (e.g. around 200 to 400 mesh).
e) The strong acid cation exchange resin may be used in the form of a column.
f) The volume of resin used (e.g. when packed in a column) may be 5 ml or less, (e.g. 0.1 to 5 ml), preferably 2 ml or less, more preferably 0.1 to 1 ml (e.g. around 0.15 ml).
g) The strong acid cation exchange resin may be DOWEX 50WX8 or equivalent resin and may optionally and preferably have a 200-400 mesh size.
h) The strong acid cation exchange resin may be pretreated with a mineral acid such as $HNO_3$.
i) The first $^{227}$Th solution eluted from the anion exchange resin in step iv) may be loaded directly onto the strong cation exchange resin.

j) The first $^{227}$Th solution eluted from the anion exchange resin in step iv) may be mixed with one or more mineral acids, such as HNO$_3$ prior to loading onto the strong cation exchange resin.

k) The first $^{227}$Th solution eluted from the anion exchange resin in step iv) may be fully or partially evaporated and optionally redissolved in a mineral acid such as HNO$_3$ prior to loading onto the strong cation exchange resin.

Step vi) of the method of the invention is optional but preferable and relates to eluting at least a part of the contaminant $^{223}$Ra and $^{227}$Ac from said strong acid cation exchange resin using a third mineral acid in aqueous solution. This step and the entities referred to therein may have the following preferable features, either individually or in any viable combination, and optionally in any viable combination with any of the features of the other steps as described herein:

a) The third mineral acid may be an acid selected from H$_2$SO$_4$, HNO$_3$ and HCl, preferably HNO$_3$;

b) The third mineral acid may be used at a concentration of 0.1 to 8 M, preferably 0.5 to 6M, more preferably 1.0 to 5M, most preferably 2 to M (e.g. around 2.5 M). This applies particularly where the second mineral acid is HNO$_3$;

c) The aqueous solution preferably does not comprise any significant amount (e.g. less than 0.1% v/v) of any alcohol selected from methanol, ethanol and isopropanol. Preferably the aqueous solution is free or substantially free of methanol;

d) The $^{223}$Ra and $^{227}$Ac may be eluted from said strong acid cation exchange resin using 1 to 200 column volumes of the third mineral acid in aqueous solution. Preferably the amount will be 1 to 100 column volumes, more preferably 10 to 25, especially around 20 column volumes.

Step vii) of the method of the invention relates to eluting $^{227}$Th from said strong acid cation exchange resin using a first aqueous buffer solution whereby to generate a second $^{227}$Th solution. This step and the entities referred to therein may have the following preferable features, either individually or in any viable combination, and optionally in any viable combination with any of the features of the other steps as described herein:

a) The first buffer solution may have a pH of between 2.5 and 6, preferably between 3.5 and 5.

b) The first buffer solution may comprise at last one acid and a salt of that acid, each in concentrations of between 0.1 and 5M, preferably between 0.5 and 3M.

c) The first buffer solution may comprise at least one organic acid and a salt of that organic acid, such as a metal or ammonium salt (e.g. a pharmaceutically tolerable salt such as sodium, potassium, calcium, and/or ammonium salt).

d) The first buffer solution may comprise or consist essentially of or consist of an acetate buffer. Preferably the acetate buffer will comprise acetic acid and ammonium acetate, most preferably each at concentrations as indicated herein (e.g. between 0.5 and 3M).

e) The second $^{227}$Th solution will preferably have a contamination level of no more than 100 (e.g. 0.0001 to 100 or 0.0001 to 40) Bq $^{227}$Ac per 1 MBq $^{227}$Th, more preferably no more than 50 Bq $^{227}$Ac per 1MBq $^{227}$Th and most preferably no more than 40 Bq $^{227}$Ac per 1 MBq $^{227}$Th;

f) The second $^{227}$Th solution will preferably have a methanol content of not more than 100 ppm per dose of $^{227}$Th, preferably no more than 50 mg, and more preferably no more than 10 ppm per dose (where a dose of $^{227}$Th is as described herein, such as 1 to 75 MBq).

g) The steps of loading the first $^{227}$Th solution onto the acid cation exchange resin and eluting the second $^{227}$Th solution may provide a separation ratio of $^{227}$Th to $^{227}$Ac of at least 10:1 (e.g. 10:1 to 10,000:1), preferably at least 100:1, more preferably at least 500:1.

h) The $^{227}$Th may be eluted from said strong acid cation exchange resin in uncomplexed form, such as in the form of a simple salt in solution.

i) The use of complexing agents such as DTPA may be avoided, and in one embodiment all solutions used in step iv) to vi) are substantially free of complexing agents.

In addition to the two-column separation method indicated above, further purification of the second $^{227}$Th solution is achieved by an additional, optional but highly preferably purification step. This purification step will typically take place directly after step vii) and typically comprises:

viii) loading the second $^{227}$Th solution eluted in step vii) onto a second strong base anion exchange resin;

ix) eluting $^{223}$Ra and/or $^{227}$Ac from said second strong base anion exchange resin using a fourth mineral acid in an aqueous solution; and x) eluting $^{227}$Th from said second strong base anion exchange resin using a fifth mineral acid in an aqueous solution to provide a third $^{227}$Th solution.

Step viii) of the method of the invention relates to the loading of the second $^{227}$Th solution eluted in step vii) onto a second strong base anion exchange resin. This step and the entities referred to therein may have the following preferable features, either individually or in any viable combination, and optionally in any viable combination with any of the features of the other steps as described herein:

a) The second strong base anion exchange resin may be a polystyrene/divinyl benzene copolymer based resin, preferably containing 1-95%; divinyl benzene b) The second strong base anion exchange resin may be an R—N$^+$Me$_3$ type (type I) resin or an R—N$^+$Me$_2$CH$_2$CH$_2$OH (Type II) resin, preferably a type I resin;

c) The strong base anion exchange resin may have an exchange capacity of 0.2 to 5 meq/ml, preferably 0.6 to 3 meq/ml, most preferably 1 to 1.5 meq/ml (e.g. around 1.2 meq/ml);

d) The second strong base anion exchange resin may have a particle size grading of 10 to 800 mesh, preferably 50 to 600 mesh, more preferably 100 to 500 mesh (e.g. around 200 to 400 mesh).

e) The second strong base anion exchange resin may be the same as the first strong base anion exchange resin.

f) The second strong base anion exchange resin may be used in the form of a column.

f) The volume of resin used (e.g. when packed in a column) may be 10 ml or less, (e.g. 0.5 to 10 ml), preferably 5 ml or less, more preferably 0.5 to 2 ml (e.g. around 0.25 ml).

g) The second strong base anion exchange resin may be DOWEX 1X8 (e.g. DOWEX AG 1X8) or equivalent resin and may optionally and preferably have a 200-400 mesh size.

h) The second $^{227}$Th solution may be acidified prior to loading on the second strong base anion exchange resin.

i) The second $^{227}$Th solution may be acidified with a mineral acid, preferably HNO$_3$.

j) The second $^{227}$Th solution may be acidified with a mineral acid at a concentration of 5 to 24M, preferably 10 to 22M, more preferably 14 to 18 M.

k) The second $^{227}$Th solution may be acidified with a mineral acid free or substantially free of any alcoholic solvent (e.g. less than 1%).

Step ix) of the method of the invention is optional but preferable and relates to eluting $^{223}$Ra and/or $^{227}$Ac from the second strong base anion exchange resin using a fourth mineral acid in aqueous solution. This step and the entities referred to therein may have the following preferable features, either individually or in any viable combination, and optionally in any viable combination with any of the features of the other steps as described herein:

a) The fourth mineral acid may be an acid selected from $H_2SO_4$ or $HNO_3$ preferably $HNO_3$.

b) The first mineral acid may be used at a concentration of 1 to 12M, such as 3 to 10 M or 5 to 9 M, preferably 7 to 8.5 M (e.g. around 8M), particularly where the fourth mineral acid is $HNO_3$.

c) The aqueous solution may be free or substantially free of any alcohol. In particular, the aqueous solution may contain less than 1% (e.g. 0 to 1%) of any alcohol selected from methanol, ethanol and isopropanol, particularly methanol;

d) The $^{223}$Ra and/or $^{227}$Ac may be eluted from said second strong base anion exchange resin using 1 to 200 column volumes of the first mineral acid in aqueous solution. Preferably the amount will be 5 to 100 column volumes (e.g. around 50 column volumes).

Step x) of the method of the invention relates to eluting $^{227}$Th from said second strong base anion exchange resin using a fifth mineral acid in an aqueous solution whereby to generate a third $^{227}$Th solution. This step and the entities referred to therein may have the following preferable features, either individually or in any viable combination, and optionally in any viable combination with any of the features of the other steps as described herein:

a) The fifth mineral acid may be an acid selected from $H_2SO_4$ and HCl, preferably HCl.

b) The fifth mineral acid may be used at a concentration of 0.1 to 8M, preferably 0.5 to 5M, more preferably 2 to 4M, most preferably around 3M. This applies particularly where the second mineral acid is HCl.

c) The third $^{227}$Th solution may be eluted from said second strong base anion exchange resin using 1 to 200 column volumes of the second mineral acid in aqueous solution. Preferably the amount will be 1 to 100 column volumes (e.g. around 50 column volumes).

d) The aqueous solution may be free or substantially free of other solvents such as alcoholic solvents (e.g. less than 1%).

e) The third $^{227}$Th solution will preferably have a contamination level of no more than 100 (e.g. 1 to 50) Bq $^{227}$Ac per 100 MBq $^{227}$Th, more preferably no more than 45 Bq $^{227}$Ac per 100 MBq $^{227}$Th (e.g. no more than 30) and most preferably no more than 5 Bq $^{227}$Ac per 100 MBq $^{227}$Th. A purity of 1 Bq $^{227}$Ac per 100 MBq $^{227}$Th or around 0.5 Bq $^{227}$Ac per 100 MBq $^{227}$Th may most desirably be achieved in the third solution;

f) The steps viii) to x) of loading the second $^{227}$Th solution onto the second base anion exchange resin, eluting $^{223}$Ra and/or $^{227}$Ac and eluting a third $^{227}$Th solution may provide a separation ratio of $^{227}$Ac to $^{227}$Th of at least 5:1 000 000 (e.g. 5:1 000 000 to 5:10 000 000), preferably at least 5:50 000 000, more preferably at least 5:100 000 000.

g) The $^{227}$Th may be eluted from said strong base anion exchange resin in uncomplexed form, such as in the form of a simple salt in solution (e.g. as the salt of the fifth mineral acid such as the chloride salt).

h) Optionally, the use of complexing agents such as DTPA may be avoided, and in one embodiment all solutions used in steps viii) to x) are substantially free of complexing agents, such as DTPA.

In addition to the above steps, the methods of the invention and all corresponding aspects may comprise additional steps, for example to validate the purity of the $^{227}$Th for pharmaceutical purposes, to exchange counter-ions, concentrate or dilute the solution or to control factors such as pH and ionic strengths. Each of these steps thus forms an optional but preferable additional step in the various aspects of the present invention.

It is preferable that the methods of the present invention provide for a high yield of the $^{227}$Th product. This is not only because of the desire to avoid wastage or a valuable product but also because all lost radioactive material forms radioactive waste which must then be disposed of safely. Thus, in one embodiment, at least 70% of the $^{227}$Th loaded in step ii) is eluted in step vii). Similarly, where steps viii) to x) are carried out, at least 70% of the $^{227}$Th loaded in step ii) is eluted in step x). These will preferably be at least 75%, more preferably at least 78% and most preferably at least 80% yields.

In the final eluted solutions (second or third) and in the $^{227}$Th product (optionally formed or formable by the methods of the invention), the $^{227}$Th may comprise less than 10 Bq $^{227}$Ac per 100 MBq $^{227}$Th. This will preferably be less than 5 Bq $^{227}$Ac per 100 MBq $^{227}$Th.

Following production by the methods described herein, the second or third $^{227}$Th solution may undergo any or all of the following optional steps for validation and preparation for distribution:

xi) Visual check of product, appearance.

xii) Dispensing of a dose into a suitable vessel such as a glass vial.

xiii) Evaporation of solvent from the solution.

ixx) Sealing, labelling and/or packaging for transport.

xx) Quality control assay/sampling, e.g. to validate for assay of $^{227}$Th content, radionuclidic identity ($^{227}$Th), radionuclidic purity, especially to confirm an acceptable level of $^{227}$Ac content and $^{223}$Ra and/or to test for bacterial endotoxins.

In a corresponding aspect of the present invention, there is additionally provided pharmaceutical composition comprising the $^{227}$Th and optionally at least one pharmaceutically acceptable diluent. Such a pharmaceutical composition may comprise $^{227}$Th of a purity indicated herein, optionally formed or formable by the methods of the present invention. Suitable carriers and diluents including water for injection, pH adjusters and buffers, salts (e.g. NaCl) and other suitable materials will be well known to those of skill in the art.

The pharmaceutical composition will comprise the $^{227}$Th as described here, typically as an ion, such as the $Th^{4+}$ ion. Such compositions may comprise a simple salt of the $^{227}$Th of the invention but will more preferably comprise a complex of the $^{227}$Th of the invention with at least one ligand, such as an octadentate 3,2-hydroxypyridinone (3,2-HOPO) ligand, a DOTA (tetraazacyclododecane-tetraacetic acid, such as 1,4,7,10-tetraazacyclododecane-1,4,7,10-tetraacetic acid) ligand and/or a NOTA (triazacyclononane-triacetic acid, such as 1,4,7-triazacyclononane-N,N',N'''-triacetic acid) ligand. Suitable ligands are disclosed in WO2011/098611, which is hereby incorporated by reference, particularly with reference to formulae I to IX disclosed therein, which represent typical suitable HOPO ligands. Such ligands may be used in themselves or conjugated to at least one targeting moiety, such as an antibody. Antibodies, antibody constructs, fragments of antibodies (e.g. FAB or F(AB)'2 fragments or any fragment comprising at least one antigen binding region(s)), constructs of fragments (e.g. single chain antibodies) or a mixture thereof are particularly preferred. The pharmaceutical compositions of the invention may thus comprise $Th^{4+}$ ion of $^{227}Th$ of pharmaceutical purity as disclosed herein, complexed to a conjugate of a ligand, such as a 3,2- hydroxypyridinone (3,2-HOPO) ligand, and at least one antibody, antibody fragment or antibody construct, plus optionally pharmaceutically acceptable carriers and/or diluents.

As used herein, the term "comprising" is given an open meaning such that additional components may optionally be present (thus disclosing both "open" and "closed" forms). In contrast the term "consisting of" is given a closed meaning only, such that (to an effective, measurable and/or absolute degree), only those substances indicated (including any optional substances as appropriate) will be present. Correspondingly, a mixture or substance described as "consisting essentially of" will in essence consist of the stated components such that any additional components do not affect the essential behaviour to any significant extent. Such mixtures may, for example, contain less than 5% (e.g. 0 to 5%) of other components, preferably less than 1% and more preferably less than 0.25% of other components. Similarly, where a term is given as "substantially", "around", "about" or "approximately" a given value, this allows for the exact value given, and independently allows for a small variability, particularly where this does not affect the substance of the property described. Such variability may be, for example ±5% (e.g. ±0.001% to 5%), preferably ±1%, more preferably ±0.25%. All % herein are given by weight unless otherwise indicated.

The invention will now be illustrated further by reference to the following non-limiting examples and the attached figures, in which:

The invention will now be illustrated further by reference to the following non-limiting examples and the attached figures, in which:

In FIG. 1 the following steps are included:

(1) Storage of the generator for in-growth of $^{227}Th$.
(2) Evaporation of the generator to dryness prior to loading
(3) Dissolution of the dry generator in methanolic nitric acid and loading onto a first anion exchange column.
(4) Elution of $^{223}Ra$ and $^{227}AC$ using nitric acid (regeneration of $^{227}Ac$ for the generator) and elution of a first $^{227}Th$ solution with HCl.
(5) Loading of the first $^{227}Th$ solution onto a cation exchange column, elution of $^{227}Ac$ and $^{223}Ra$ with nitric acid (to waste) and elution of a second $^{227}Th$ solution with acetate buffer.
(6) Acidification of the second $^{227}Th$ solution with concentrated nitric acid and loading onto a second anion exchange column.
(7) Elution of $^{227}AC$ and $^{223}Ra$ with nitric acid (to waste) and elution of a third $^{227}Th$ solution with HCl.
(8) Dispensing of $^{227}Th$ does into glass vials
(9) Evaporation of the third $^{227}Th$ solution to leave $^{227}Th$ chloride (10) Quality control of the $^{227}Th$ chloride drug substance.

EXAMPLES

Example 1—Outline of Typical Process

The thorium-227 is generated by natural decay of actinium-227. The separation and purification to form the radionuclide component thorium-227 chloride, is performed in a dedicated manufacturing line for thorium-227 chloride.

The starting material in the manufacturing process of the thorium-227 chloride is actinium-227 in nitric acid solution (A-generator).

A-generators are stored for in-growth of thorium-227 in-between manufacturing of thorium-227 chloride batches, and are used repeatedly for the manufacturing of thorium-227 chloride. The amount of actinium-227 in the A-generator and the in-growth time for the A-generator used, will determine the radioactivity level in the resulting thorium-227 chloride batch. Solid phase extraction (SPE) on anion and cation exchange resins are applied to separate thorium-227 from its predecessor nuclide actinium-227 and to further remove radium-223 and radium-223 daughters.

The manufacture of thorium-227 consists of the following steps:
1) Storage for in-growth of thorium-227
2) Evaporation to Dryness
3) Dissolution
4) Thorium-227 Separation
5) Thorium-227 Purification #1
6) Acidification of Thorium-227 eluate from Purification #1
7) Thorium-227 Purification #2
8) Dispensing of thorium-227 eluate
9) Evaporation by heat
10) Testing and Release The separation step on the first anion exchange SPE cartridge (step 4) is based on the formation of negatively charged complexes of thorium-227 with the eluent solution and the trapping of these negatively charged complexes on the first anion exchange SPE cartridge, whereas actinium-227 and radium-223 pass through the resin under the conditions applied and are regenerated back into the A-generator. The thorium-227 eluate from the anion exchange SPE cartridge is loaded on to a cation exchange SPE cartridge (second cartridge—step 5). This is followed by further purification on an additional anion exchange SPE cartridge (third cartridge—step 7).

The second and third SPE cartridges are used mainly to remove residual amounts of actinium from the first thorium-227 eluate which passed the first purification cartridge. For these separation and purification steps, raw material solutions and premixed raw material solutions with specified volumes are used to minimize the number of handling steps and in-process controls. During the process these solutions are applied, trapped and eluted, as in solid phase extraction, with no selection of fractions at any of the three separation/purification steps. The final purified thorium-227 eluate is dispensed into vials and evaporated by heat to form a film of thorium-227 chloride.

Example 2—Batch Purification

Data from one $^{227}Th$ batch of 110 MBq vials is provided in the below table.

| Test | Batch no. A503001 |
|---|---|
| Appearance | No visible liquid |
| Radionuclidic identity (RNI) (thorium-227) | Complies |
| Radionuclidic purity (RNP) Actinium-227 | Not detected, LT 0.001% |
| Radionuclidic purity (RNP) Radium-223 | LT 0.2% |
| Assay thorium-227 | 110 MBq/vial |
| Bacterial endotoxins | LT 5 EU/vial |
| Date of manufacture | 2015 Mar. 9 |
| Actinium-227 used | 3800 MBq |
| Ingrowth | 75% |
| Thorium-227 produced | 2280 MBq |
| Throiium-227 yield | 80% |
| Batch size | 18 vials |

EU = Endotoxin Unit;
LT = Less Than

The invention claimed is:

1. A method for the generation of $^{227}$Th of pharmaceutically tolerable purity, comprising:
   i) preparing a generator mixture comprising $^{227}$Ac, $^{227}$Th and $^{223}$Ra;
   ii) loading said generator mixture onto a strong base anion exchange resin;
   iii) eluting a mixture of said $^{223}$Ra and $^{227}$Ac from said strong base anion exchange resin using a first mineral acid in an aqueous solution;
   iv) eluting $^{227}$Th from said strong base anion exchange resin using a second mineral acid in an aqueous solution whereby to generate a first $^{227}$Th solution containing contaminant $^{223}$Ra and $^{227}$Ac;
   v) loading the first $^{227}$Th solution onto a strong acid cation exchange resin;
   vi) eluting at least a part of the contaminant $^{223}$Ra and $^{227}$Ac from said strong acid cation exchange resin using a third mineral acid in aqueous solution;
   vii) eluting the $^{227}$Th from said strong acid cation exchange resin using a first aqueous buffer solution to provide a second $^{227}$Th solution;
   viii) loading the second $^{227}$Th solution eluted in step vii) onto a second strong base anion exchange resin;
   ix) eluting $^{223}$Ra and/or $^{227}$Ac from said second strong base anion exchange resin using a fourth mineral acid in an aqueous solution;
   x) eluting $^{227}$Th from said second strong base anion exchange resin using a fifth mineral acid in an aqueous solution to provide a third $^{227}$Th solution; and
   y) storing the $^{227}$Ac eluted in step iii) for a period sufficient to allow ingrowth of $^{227}$Th by radioactive decay, whereby to regenerate a generator mixture comprising $^{227}$Ac, $^{227}$Th and $^{223}$Ra,
   wherein the second $^{227}$Th solution has a contamination level of no more than 200 Bq $^{227}$Ac per 1 MBq $^{227}$Th.

2. The method of claim 1, wherein a $^{227}$Th radioactivity of at least 50 MBq is employed in step i).

3. The method of claim 1, wherein the strong base anion exchange resin and the second strong base anion exchange resin comprise the same base moieties.

4. The method of claim 1, wherein the strong base anion exchange resin is a polystyrene/divinyl benzene copolymer based resin.

5. The method of claim 1, wherein the strong base anion exchange resin and the second strong base anion exchange resin is independently an R—N$^+$Me$_3$ type (type I) resin or an R—N$^+$Me$_2$CH$_2$CH$_2$OH (Type II) resin.

6. The method of claim 1, wherein the first mineral acid is an acid selected from H$_2$SO$_4$, HNO$_3$ and mixtures thereof.

7. The method of claim 1, wherein the first mineral acid is used at a concentration of 1 to 12 M.

8. The method of claim 1, wherein the second mineral acid is an acid selected from H$_2$SO$_4$ and HCl.

9. The method of claim 1, wherein the second mineral acid is used at a concentration of 0.1 to 8 M.

10. The method of claim 1, wherein the strong acid cation exchange resin is a polystyrene/divinyl benzene copolymer based resin.

11. The method of claim 1, wherein the strong acid cation exchange resin is of SO$_3$H type.

12. The method of claim 1, wherein the third mineral acid is an acid selected from H$_2$SO$_4$, HNO$_3$ and HCl.

13. The method of claim 1, wherein the third mineral acid is used at a concentration of 0.1 to 8 M.

14. The method of claim 1, wherein the buffer solution has a pH of between 2.5 and 6.

15. The method of claim 1, wherein the buffer solution is an acetate buffer.

16. The method of claim 1, wherein the buffer solution does not comprise any significant amount of any alcohol selected from methanol, ethanol and isopropanol.

17. The method of claim 1, wherein said generator mixture is dissolved in an alcoholic aqueous solution comprising a loading mineral acid prior to loading said generator mixture onto a strong base anion exchange resin in step ii).

18. The method of claim 1, wherein step viii) comprises acidifying the second $^{227}$Th solution prior to loading onto said second strong base resin.

19. The method of claim 1, wherein said fourth mineral acid is an acid selected from H$_2$SO$_4$, HNO$_3$ and HCl.

20. The method of claim 1, wherein said fourth mineral acid is used at a concentration of 1 to 12 M.

21. The method of claim 1, wherein the fifth mineral acid is an acid selected from H$_2$SO$_4$ and HCl.

22. The method of claim 1, wherein the fifth mineral acid is used at a concentration of 0.1 to 8 M.

23. The method of claim 4, wherein the polystyrene/divinyl benzene copolymer based resin of the strong base anion exchange resin contains 1 to 95% divinyl benzene.

24. The method of claim 10, wherein the polystyrene/divinyl benzene copolymer based resin of the strong acid cation exchange resin contains 1 to 95% divinyl benzene.

25. The method of claim 12, wherein the third mineral acid is HNO$_3$.

26. The method of claim 16, wherein the buffer solution does not comprise any significant amount of methanol.

27. The method of claim 19, wherein the fourth mineral acid is HNO$_3$.

28. The method of claim 21, wherein the fifth mineral acid is HCl.

* * * * *